United States Patent [19]
Kraus et al.

[11] Patent Number: 5,925,567
[45] Date of Patent: *Jul. 20, 1999

[54] SELECTIVE EXPANSION OF TARGET CELL POPULATIONS

[75] Inventors: Morey Kraus, Worcester; Paul T. Wilder, Boylston, both of Mass.; Jill Friberg, Seattle, Wash.

[73] Assignee: t. Breeders, Inc., Worcester, Mass.

[*] Notice: This patent is subject to a terminal disclaimer.

[21] Appl. No.: 08/944,755

[22] Filed: Oct. 6, 1997

Related U.S. Application Data

[63] Continuation-in-part of application No. 08/446,165, May 19, 1995, Pat. No. 5,674,750.
[51] Int. Cl.$^6$ ................................ C12N 5/02; C12N 5/08
[52] U.S. Cl. .............................. 435/372; 435/2; 435/374; 435/377; 435/395; 435/402; 435/403
[58] Field of Search ................................ 435/2, 402, 372, 435/375, 374, 377, 395, 403

[56] References Cited

U.S. PATENT DOCUMENTS

| | | |
|---|---|---|
| 4,514,499 | 4/1985 | Noll . |
| 4,714,680 | 12/1987 | Civin . |
| 4,965,204 | 10/1990 | Civin . |
| 5,004,681 | 4/1991 | Boyse et al. . |
| 5,035,994 | 7/1991 | Civin . |
| 5,061,620 | 10/1991 | Tsukamoto et al. . |
| 5,399,493 | 3/1995 | Emerson et al. . |
| 5,460,964 | 10/1995 | McGlave et al. . |
| 5,472,867 | 12/1995 | Kanz et al. . |
| 5,486,359 | 1/1996 | Caplan ................................ 424/93.7 |
| 5,635,386 | 6/1997 | Palsson et al. . |
| 5,635,387 | 6/1997 | Fei et al. . |
| 5,646,043 | 7/1997 | Emerson et al. . |

FOREIGN PATENT DOCUMENTS

WO 96/36696 11/1996 WIPO .

OTHER PUBLICATIONS

"Reconstitution of Hematopoiesis after High–Dose Chemotherapy by Autologous Progenitor Cell Generated Ex Vivo", by Wolfram Brugger, MD et al., The New England Journal of Medicine, vol. 333, No. 5,, Aug. 3, 1995, pp. 283–287.

"Identification of Primitive Human Hematopoietic Cells Capable of Repopulating NOD/SCID Mouse Bone Marrow: Implications for Gene Therapy", Nature Medicine, vol. 2, No. 12, Dec. 1996, pp. 1329–1337.

Expansion in vitro of Transplantable Human Cord Blood Stem Cells Demonstrated Using a Quantitative Assay of Their Lympho–myeloid Repopulating Activity in Nonobese Diabetic–scid/scid Mice, Proc. Natl. Acad. Sci. USA, vol. 94, Sep. 1997, pp. 9836–9841.

"Quantative Analysis Reveals Expansion of Human Hematopoietic Repopulating Cells After Short–term Ex Vivo Culture", J. Exp. Med., The Rockefeller University Press, vol. 186, No. 4, Aug. 18, 1997, pp. 619–624.

Hsiung, GD, Hsiung's Diagnostic Virology, 4th ed. Yale Univ. Press, New Haven, CT, pp. 20–22, 1994.

Johnstone et al. Immunochemistry in Practice, 2nd edition, Blackwell Scientific Publications, Osney Mead. Oxford OX30EL pp. 242–243, 1987.

Mayani et al. (1993) Blood. Vo. 81(12):3252–3258.

*Primary Examiner*—David Saunders
*Assistant Examiner*—Mary Beth Tung
*Attorney, Agent, or Firm*—Fish & Richardson P.C.

[57] ABSTRACT

A method is provided for selective expansion of a predetermined target population of cells, including (a) introducing a starting sample of cells into a growth medium; (b) causing cells of the predetermined target cell population to divide; and (c) concurrently with, intermittently during, or following step (b) contacting the starting cells with a selection element, comprising a plurality of selective binding molecules with specific affinity either for target cells or for non-target cells to select cells of said predetermined target population from other cells in the growth medium. Systems are provided for selective expansion and methods of treating patients with cell populations and products.

24 Claims, 13 Drawing Sheets

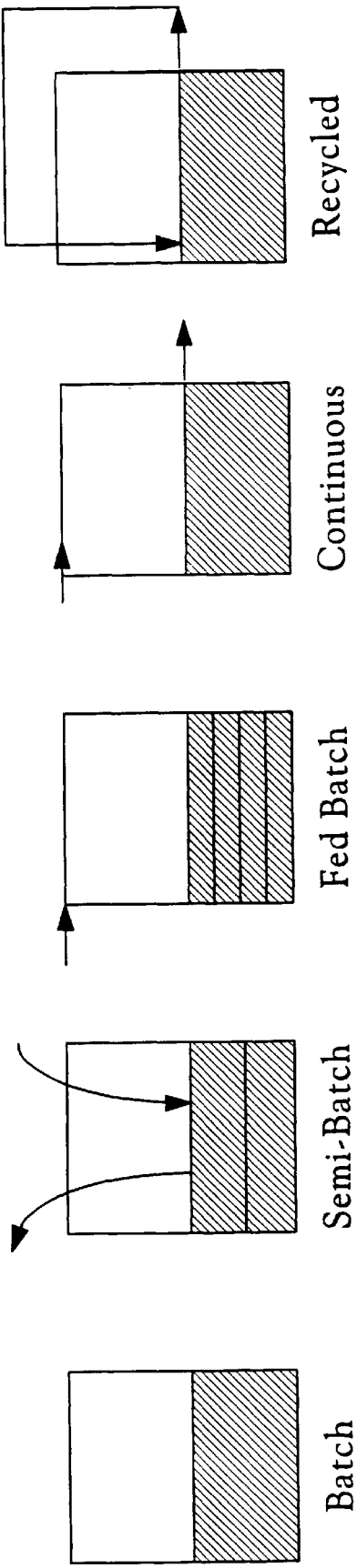

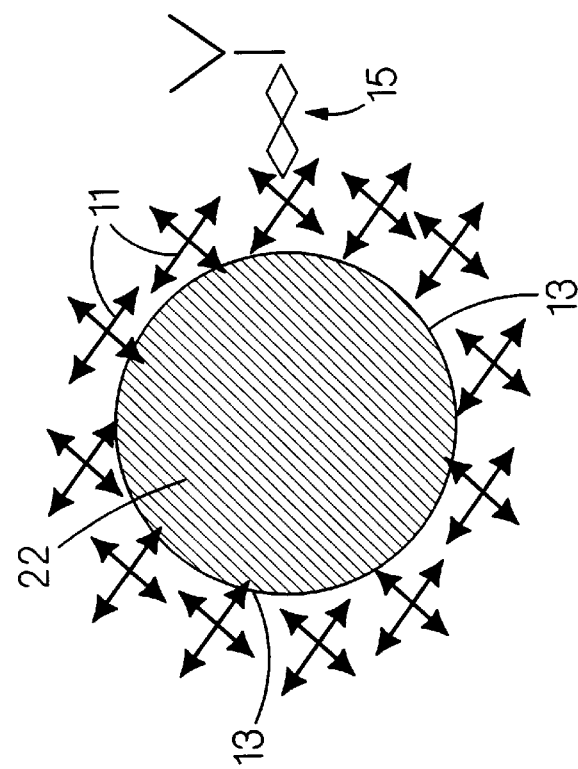
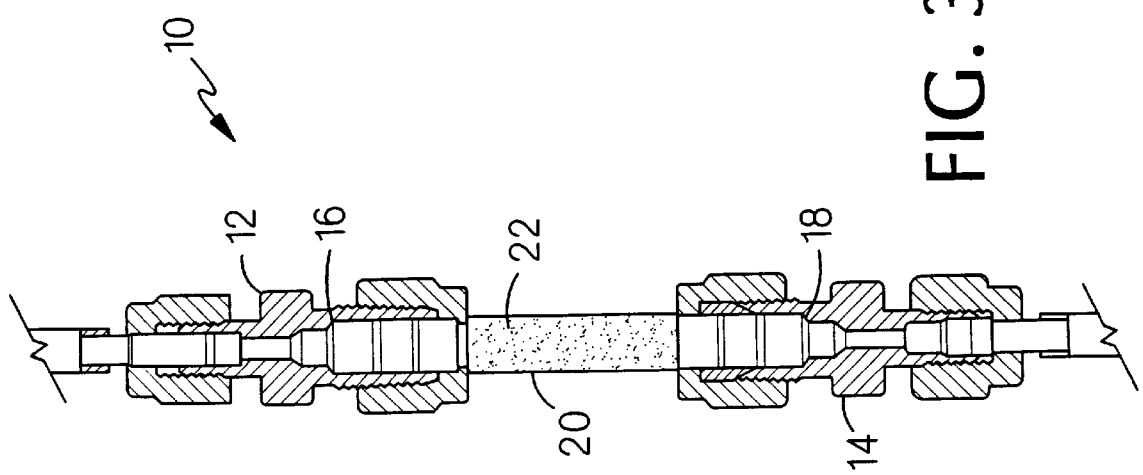

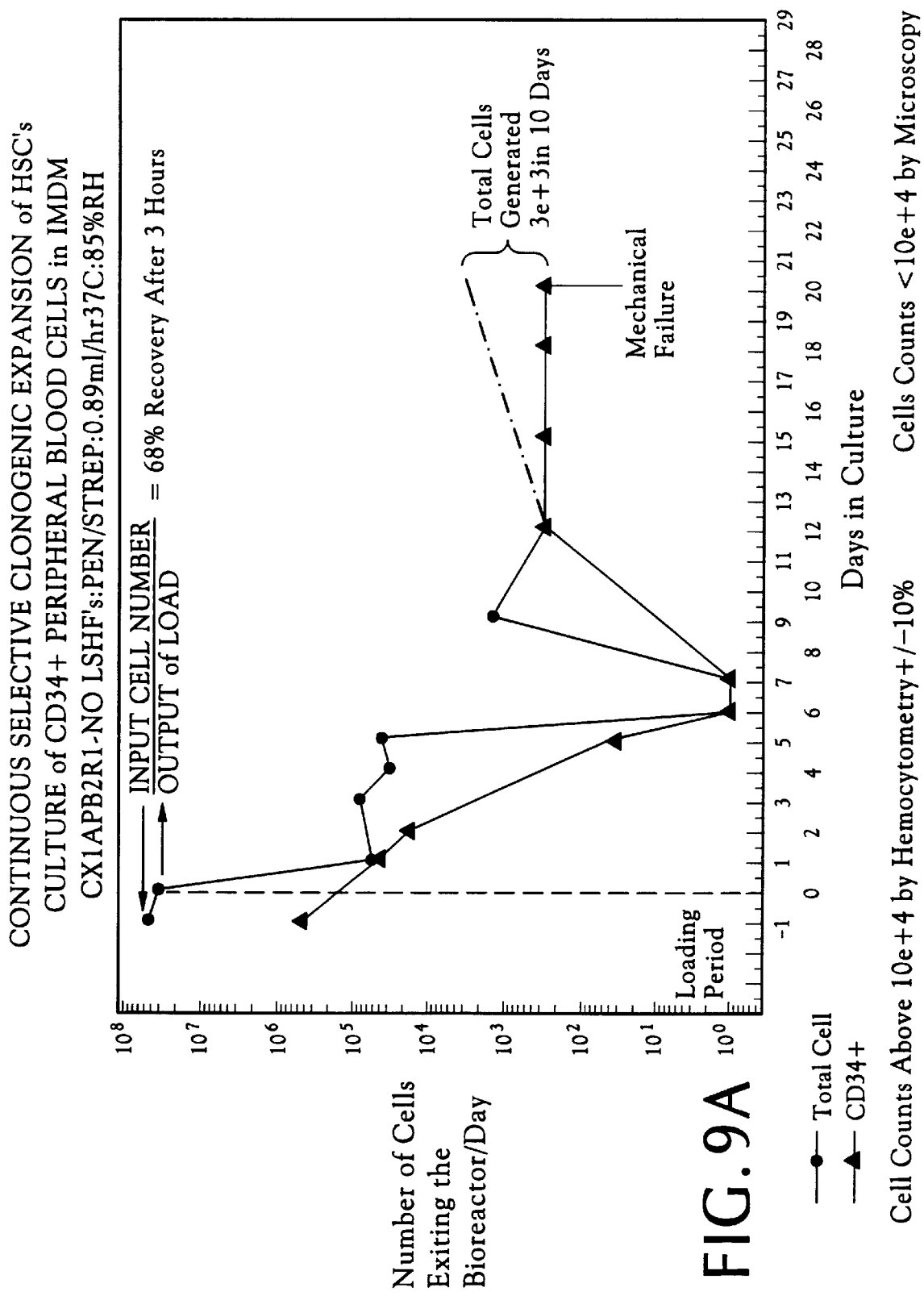

SELECTIVE EXPANSION OF TARGET CELL POPULATIONS

CROSS-REFERENCE TO RELATED APPLICATION

This application is a continuation-in-part of U.S. Ser. No. 08/446,165, filed May 19, 1995 U.S. Pat. No. 5674,750.

BACKGROUND OF THE INVENTION

This invention relates to systems for expansion of cell populations.

The origin of all the cells in blood and in the immune system is the hematopoietic stem cell (HSC). Each HSC has the potential to differentiate into at least eight separate blood cell lineages within the myeloid and lymphoid blood cell compartments. It has been estimated through successive generational analysis that one HSC has the potential to produce up to fifty million differentiated progeny. See U.S. Pat. No. 5,061,620, the disclosure of which is incorporated herein by reference in its entirety.

This enormous potential could be exploited if, starting from a small number of HSCs, a large pool of HSCs could be grown in culture without significant differentiation during expansion. This pool of HSCs could then be used to restore or supplement an immune system and/or blood forming system compromised by, e.g., radiation or chemotherapy. The pool would also be a valuable tool in the design, development and testing of diagnostic and therapeutic agents used in the treatment of immune system and/or blood forming disorders.

Efforts have been made to develop a system that would grow HSCs ex vivo and control cell proliferation and differentiation. Typically, these efforts have involved batch culture of a mixed population of cells that have been initially separated from a relatively large volume of blood.

SUMMARY OF THE INVENTION

The invention is based on our discovery that a predetermined target population of cells, in particular renewable cells, e.g., relatively undifferentiated cells including HSCs, can be clonogenically expanded in a system that either (a) positively selects for cells of the target population, or (b) negatively selects out non-target cells. Selection of this type occurs concurrently with cell growth or intermittently during cell growth. Advantageously, by selectively controlling the relative populations of cells in the system, the invention allows greater expansion of the target population. This selective population control reduces feedback inhibitions, influences factor and substrate consumption rates, and minimizes other limiting factors that tend to occur in conventional batch cultures.

In one aspect, the invention features a method of selective expansion of a predetermined target population of cells that includes: (a) introducing a starting sample of cells into a growth medium; (b) causing cells of said predetermined target cell population to divide; and (c) contacting the cells in the growth medium with a selection element, comprising a plurality of selective binding molecules with specific affinity for a predetermined population of cells, so as to select cells of said predetermined target population from other cells in the growth medium. The selection element may use positive selection (the selective binding molecules are specific for target cells), or negative selection (the selective binding molecules are specific for non-target cells). The method may also include contacting the starting cells with a reverse selection element employing the opposite type of selection.

In preferred embodiments, the starting sample of cells includes target cells, and the expansion is clonogenic. Alternatively, the starting sample of cells includes progenitors of said target cells. In some preferred embodiments, the selection element comprises a solid support to which said selective binding molecules are bound. The growth medium can be disposed in or caused to flow through a chamber. The growth medium may also be caused to recycle through the chamber, flowing from an inlet, through the chamber, to an outlet of the chamber, and returning from the outlet to the inlet via a conduit. It is further preferred that the oxygen saturation of the growth medium be regulated to be from 0% to 20% relative to the solubility of oxygen in said fluid at equilibrium with air at 37° C. and 1 atm pressure.

The invention also features a method of selective expansion of a predetermined target population of cells including: (a) introducing fluid containing a plurality of cells into a growth medium; (b) causing cells of said predetermined target cell population to divide; and (c) selecting cells of said predetermined target population from other cells in the growth medium; wherein steps (b) and (c) are carried out substantially simultaneously.

The invention also features a system for continuous selective expansion of a predetermined target population of cells. The system includes (a) a growth medium for supporting cell division; (b) a chamber for receiving said growth medium; and (c) a selection element, positioned to contact said growth medium during or after cell division. The selection element includes a plurality of binding sites bearing a selective binding molecule. The selective binding molecule can have (i) a specific affinity for cells of said predetermined target cell population or (ii) a specific affinity for non-target cells and substantially less affinity for target cells. If desired, the system can further include a reverse selection element having the opposite type of affinity.

One system of the invention for continuous selective clonogenic expansion of relatively undifferentiated cells includes: (a) a tube containing a plurality of beads of a size which permits a plurality of the undifferentiated cells to grow thereon, the beads bearing on their surfaces a plurality of selective binding molecules capable of binding to a surface antigen present on the relatively undifferentiated cells, wherein the surface antigen is not present on relatively differentiated cells; (b) means for continuously providing nutrients to the relatively undifferentiated cells growing on the beads, wherein the nutrients are delivered via a fluid which flows through the tube and past the beads so that the relatively undifferentiated cells in the tube divide and at least a portion of relatively undifferentiated cells exit the tube with the fluid; and (c) means for continuously harvesting the portion of the relatively undifferentiated cells that exit the tube.

The invention can be used to provide stem cells (HSCs) useful for enhancing the immune system of a patient. The patient's blood or bone marrow is withdrawn (or an allogeneic stem-cell containing sample is provided); stem cells are expanded and harvested according to the invention; and then those cells are re-introduced into the patient, where they will facilitate enhancement or reconstitution of the patient's immune and/or blood forming system.

Preferably, the sample taken from the patient is relatively small, e.g., less than about 100 to 200 ml, to minimize trauma to the patient. The preferred potency and dosage of the undifferentiated cells to administer to the patient, and duration of administration, will vary depending upon the condition of the patient's immune or blood forming system, but would generally be expected to be in the range of from about 100 to $1 \times 10^6$ cells/kg body wgt/dose/day.

Alternatively, the invention can be used to provide to a patient a predetermined population of relatively differentiated cells, by providing a sample containing a population of cells which cells are the progenitor to the predetermined population, and using the system of the invention to cause the progenitor cells to proliferate and differentiate to form the predetermined population of cells, e.g., by providing the cells with a growth factor which will cause differentiation. For example, the differentiated cells may be lymphoid precursors, myeloid precursors or erythroid precursors. The invention can also be used to provide to a patient a therapeutic compound produced by a population of cells by using the system of the invention to proliferate cells of the population and to cause the population to produce the substance.

The term "continuous," as used herein, refers to a process which proceeds substantially constantly, with dividing cells being removed from the system shortly after they are born, rather than remaining in culture as in a conventional batch process. This term, as used herein, does not imply that the process is necessarily a steady state process, although in some preferred embodiments steady state may potentially be reached.

The term "specific affinity," as used herein, refers to a tendency to bind a surface molecule or feature that is present on a distinct population of cells and absent on cells not of the population. Examples of such surface molecules or features include but are not limited to cell adhesion molecules, antigens, carbohydrates and functional or non-functional receptors.

The term "non-specific interaction," as used herein, refers to interactions which interfere with and/or reduce the efficiency of desired specific interactions.

The invention provides tremendous potential for continuous long-term production of cell populations which can be supplied to a patient or other user of the cells almost as soon as the cells are born (or frozen as soon as they are harvested and supplied in frozen form at any desired time). The system can be used as a research tool for studying the effects of biopharmacological agents, growth factors, mitogens and the like, and also as a diagnostic tool, e.g., to gauge the hematopoietic potential of a patient.

The invention can be used not only to proliferate relatively undifferentiated cells, but also to produce populations of other cells simply by selecting the appropriate growth factor to supply to the system during expansion, and to produce desired cell by-products, e.g., those which could be administered as therapeutic compounds to a patient. Because the initial cell sample can be autologous, the cell populations or cell by-products produced are likely to be readily accepted by the patient from whom the cell sample was obtained.

Because the contents of the system can be frozen, a sample can be taken from a patient, introduced into the system, and then saved for a prolonged period for later use when needed, e.g., when the patient's immune system or blood forming system is challenged.

Other features and advantages of the invention will be apparent from the following detailed description, and from the claims.

BRIEF DESCRIPTION OF THE DRAWINGS

FIGS. 2–2d are schematic diagrams illustrating alternative modes of operation of systems according to different embodiments of the invention.

FIG. 3 is a somewhat schematic cross-sectional side view of a bioreactor suitable for use in the continuous mode of operation shown in FIG. 2c or the recycle mode shown in FIG. 2d. FIG. 3a is a highly enlarged, diagrammatic view of a bead used in the bioreactor of FIG. 3.

FIGS. 9 and 9a are graphs illustrating, respectively, the results obtained from the experiments described in Examples 1 and 2.

DETAILED DESCRIPTION OF PREFERRED EMBODIMENTS

As discussed above, the invention broadly features a method of substantially continuously proliferating cells of a desired target population by providing a system containing a nutrient medium in which cell proliferation can occur, and selecting cells of the target population from non-target cells in the system, concurrently with proliferation, intermittently during proliferation or following proliferation. Cell proliferation and cell selection can be carried out using an almost infinite variety of different techniques and settings, of which only a few are described below by way of example. Many other techniques will be readily perceived by those skilled in the art.

All of the preferred techniques, however, are based on the concepts of positive selection (providing a selection element having an affinity for, i.e., "selecting", target cells) and negative selection (providing a selection element having an affinity for, i.e., "selecting", non-target cells). These two techniques, used alone or in combination, allow unwanted cells to be removed from the system and target cells to be harvested whenever desired.

Figure 1:
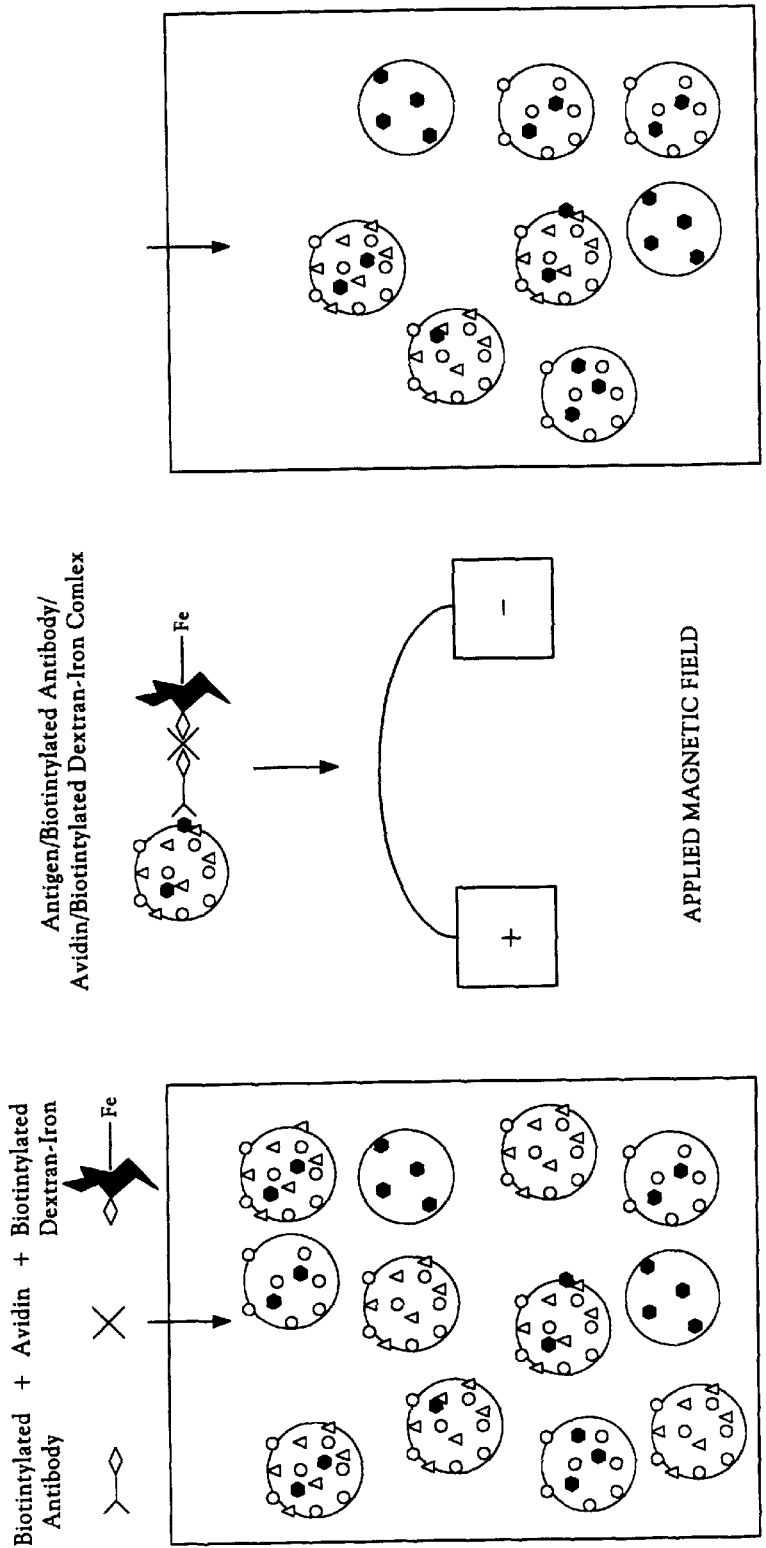
FIG. 1 is a highly enlarged diagrammatic view illustrating a method of positive selection of a target cell.

An example of a positive selection technique is illustrated diagrammatically in FIG. 1. Briefly, one or more biotintylated antibodies, specific for the target cells, and avidin are sequentially introduced into the system. After a specified incubation time any biotintylated antibody and avidin which have not formed a complex with the target cells are rinsed away. Biotintylated dextran-iron is then added to the cell suspension. The biotintylated dextran-iron reacts with the Avidin/Biotintylated Antibody/Antigen Complex. This suspension is then passed through a magnetic field. Positively selected cells remain in the magnetic field while cells which do not have the iron conjugated complex are removed. After capture and rinsing the magnetic field is removed and the positively selected predetermined target population is returned to the nutrient medium.

Figure 1A:
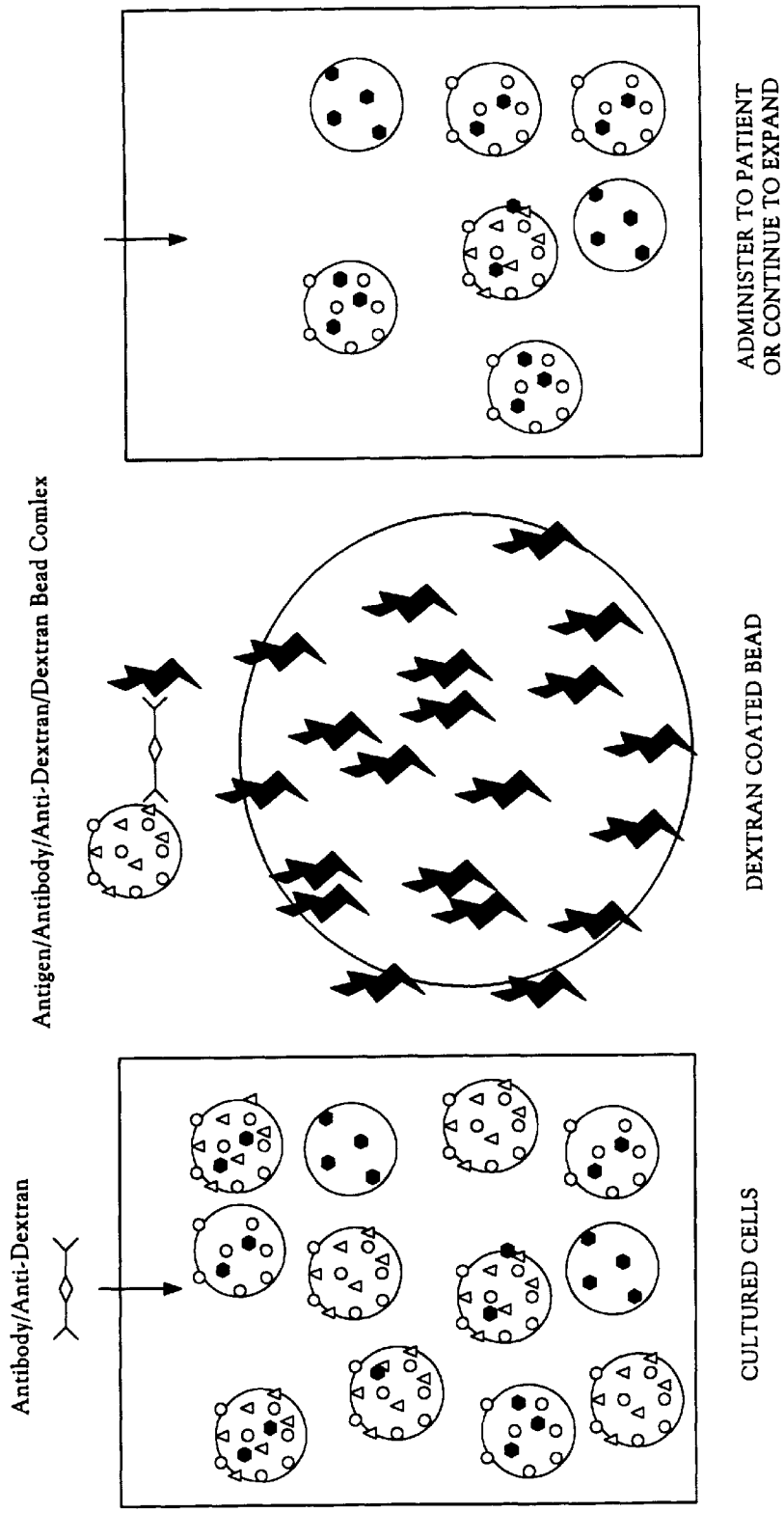
FIG. 1a is a highly enlarged diagrammatic view illustrating a method of negative selection (selection of a non-target cell).

An example of a negative selection technique is illustrated diagrammatically in FIG. 1a. Briefly, one or more anti-dextran conjugated antibodies specific for a predetermined population which is not of the predetermined target population is introduced into the culture. After a specified incubation time the cell suspension is passed through a column containing dextran coated glass beads. An Antigen/Antibody/Anti-dextran/Dextran/Bead Complex forms, removing cells not of the predetermined target population from the nutrient medium. The predetermined target population is collected downstream and returned to the nutrient medium.

Clearly, many other techniques could be utilized for both positive and negative selection, as long as the desired affinity is provided by the selection element.

The selection element can be simply the selection molecule itself, or can include other components, e.g., a solid support onto which the selection molecule is bound. The solid support can be formed of a material that will aid in performing the selection or in maintaining the selection molecules in a desired position or introducing and removing them from the system. For example, as described above with reference to FIG. 1, the selection molecule can be bound to iron or other magnetic particles to allow the selected cells to be easily removed from the system by application of a magnetic field and then collected by removal of the magnetic field. Alternatively, the selection molecules can be bound onto the wall of a vessel containing the nutrient medium, or of a chamber through which the nutrient medium flows during the method. Glass or other inert, impermeable beads can also be used as a solid support, as will be discussed in detail below. If beads or other particles are used, they can be provided in a packed configuration, through which the nutrient medium flows, or can be introduced into the system in a loose form, suspension, or in any desired type of array. As will be readily understood, a wide variety of other solid supports can be used.

As shown in FIGS. 2–2d, the selection element can be used in a variety of modes of operation in which nutrient media is supplied to and removed from the system in different manners. These modes of operation range from a selective batch culture (FIG. 2), in which nutrient media is supplied at the beginning of cell proliferation and is neither added to nor removed, to continuous flow or recycled flow cultures (FIGS. 2c and 2d, respectively) in which either fresh or recycled nutrient media flows through the system substantially continuously. These alternative modes will be discussed in detail below.

In a selective batch culture (FIG. 2), a nutrient medium is introduced into a vessel, and a starting sample of cells is also introduced into the vessel. During cell proliferation, nutrient medium is neither introduced nor removed. However, selected cells are physically selected, i.e., separated from other cells in the nutrient medium by binding to a selection element, either continuously, intermittently or following cell proliferation. These selected cells may be cells of a target population, if positive selection is used, or unwanted cells, if negative selection is used. Dual (positive and negative) selection can be accomplished by providing positive selection molecules on the surface of the vessel, beads, baffles, impellers, etc. while removing unwanted cells by negative selection. Alternately, cells may be positively or negatively selected outside of the culture vessel and then returned.

The selective semi-batch (2a) and selective fed batch (2b) modes of operation are similar to the selective batch mode with regard to positive and negative selection. The significant difference between these three modes is in the treatment of the nutrient medium. While in the batch mode the volume of the medium remains constant and the medium is not refreshed (it may be supplemented), the semi-batch mode allows for a partial refreshment of spent medium with new medium and the fed batch mode allows for an incremental increase in the medium volume over time.

Cell growth and selection can also be performed in a continuous (FIG. 2c) or recycling (FIG. 2d) mode of operation. In these two modes, the system includes a chamber having an inlet and an outlet, and nutrient media is caused to flow through the chamber from the inlet to the outlet. In continuous mode, new nutrient media flows through the chamber from a source or reservoir, while in recycling mode the same nutrient media is cycled through the chamber repeatedly. If desired, a system can be configured to be run alternatively in either continuous or recycling mode. Any desired selection element can be used in these modes of operation.

The following sections describe a bioreactor that is suitable for use as the chamber and selection element in the "continuous" (FIG. 2c) and "recycling" (FIG. 2d) modes of operation described above. This description is intended merely as an example of one suitable type of chamber/selection element.

Bioreactor

Referring to FIG. 3, bioreactor 10 includes two reducing union connectors 12, 14, mesh grids 16, 18 disposed in the orifice of each reducing union, and a culture column 20, disposed between the two mesh grids 16, 18, containing surface activated beads 22. Mesh grids 16, 18 retain the beads in the culture column 20.

Prior to use of the bioreactor, a coupling agent 11 is bound to the activated sites 13 at the surface of the bead 22, and a selective binding molecule 15, selected to bind a surface antigen present on relatively undifferentiated cells but not on relatively differentiated cells, is in turn bound to the coupling agent 11, forming the surface layer shown schematically in FIG. 3a. The coupling agent is provided between the selective binding molecule and the activated site in order to control the stereospecific orientation in which the selective binding molecule extends from the bead surface. It has been found that, by providing the coupling agent, more desirable orientations can be obtained. However, the selective binding molecule 15 can be bound directly to the surface of the bead if the orientation of the selective binding molecule is not a concern, e.g., if enough activation sites are provided that a sufficient number of molecules will have an orientation which will bind the relatively undifferentiated cells.

The manner in which the coupling agent and selective binding molecule are bound to the beads during manufacture of the culture column, to form the structure shown in FIG. 3a, is described in detail in the "Bioreactor Setup" and "Examples" sections below.

Bioreactor Set-Up

Before cell proliferation, described in the "Bioreactor Use" section, below, can begin, it is necessary to prepare the bioreactor by binding the coupling agent and selective binding molecule to the surface of the beads in the bioreactor, to form the bead surface shown diagrammatically in FIG. 3a (i.e., to prepare the beads to bind the cells to be proliferated).

Figure 5:
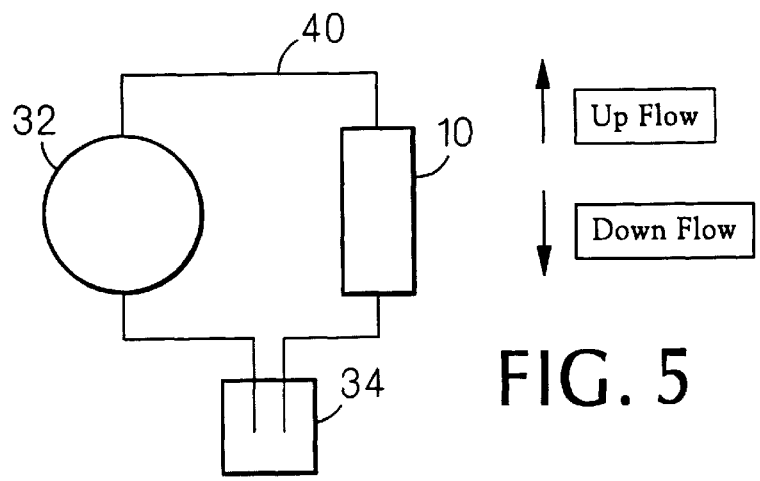
FIG. 5 is a schematic diagram showing the bioreactor during initial cycling with reagent.
Figure 6:
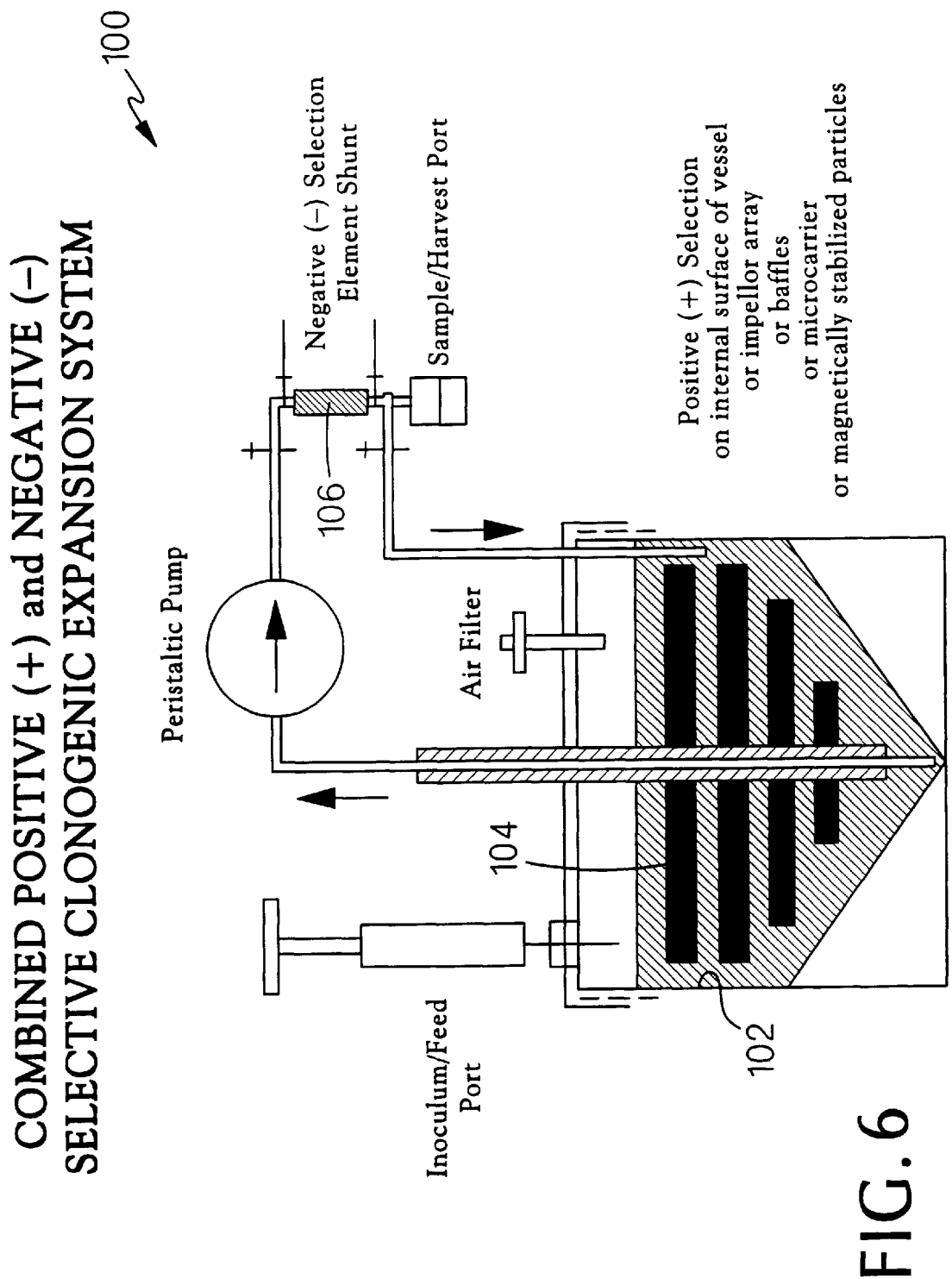
FIG. 6 is a schematic diagram showing a system including a recycle loop and both positive and negative selection elements.

The coupling agent is applied by recycling a solution of the coupling agent through the bioreactor while the bioreactor is connected in the configuration shown in FIG. 5 (a cycling configuration). After the coupling agent has been cycled through the bioreactor for sufficient time to cause the coupling agent to bind to substantially all of the activated sites on the beads (see, for example, the procedure described in Example 1, below), the column is rinsed, as shown in FIG. 6, to remove excess coupling agent which is not strongly bound to the beads. The selective binding molecule is then applied in the same manner as the coupling agent (see FIG. 5) and the column is again rinsed (see FIG. 6).

After the coupling agent and selective binding molecule have been applied to the beads, a plasma or plasma solution, preferably autologous or blood type cross-matched plasma, is applied in a similar manner. Preferably, the plasma is cycled through the bioreactor for about 4–6 hours. It is believed that a component of the plasma functions to coat any areas of the beads which are not coated with the other reagents, thus preventing non-specific interaction between the beads and undesirable cell populations. The effect of the plasma on non-specific interaction is shown graphically in FIG. 8. Other reagents can be used instead of plasma, provided that they bind to the bead surface, do not promote cell differentiation, and do not promote nonspecific interaction.

Preferably, substantially all of the plasma (except for the small portion that is apparently bound to the beads) is rinsed from the column prior to use. However, if non-specific interaction increases in the bioreactor during use, due to washing off of the plasma coating, it may be desirable to introduce a small amount of plasma, or a reagent which would function in a similar manner, to prolong the life of the column. Also, if may be desirable to include plasma in the growth medium.

During the bioreactor set-up steps described above, the incubator is preferably maintained at the same conditions described above for the cell proliferation process.

Bioreactor Use

Figure 4:
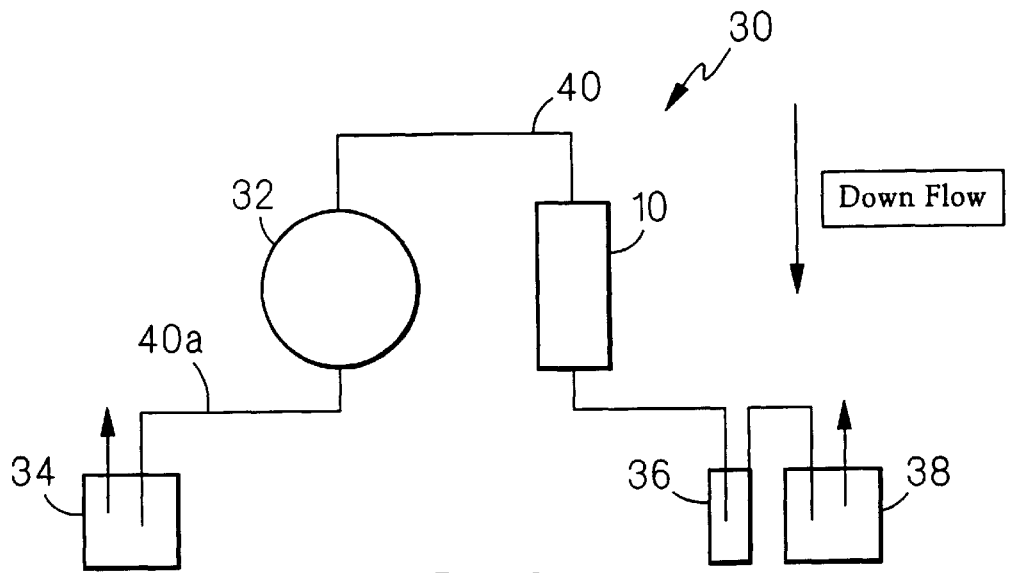
FIG. 4 is a schematic diagram showing the bioreactor in use for cell proliferation in the continuous mode of operation.

To use the bioreactor described above for stem cell expansion and harvesting, the bioreactor 10 is placed in a cell proliferation system 30, shown schematically in FIG. 4. Cell proliferation system 30 includes a peristaltic pump 32 to provide flow of fluid through the system, a reagent reservoir 34, a sampler tube 36, a waste reservoir 38, and tubing 40 connecting these components in the illustrated arrangement. The cell proliferation system 30 is disposed within an incubator 31 (e.g., an incubator commercially available under the tradename NuAire NU-2700) which is maintained at approximately 37±2 degrees C., 85–90% RH and 5% $CO_2$ throughout the cell proliferation process.

To use the bioreactor system, a sample containing CD34+ cells, e.g., Ficoll-Paque Gradient Purified Mononuclear Fraction (MNF) (approx. $5 \times 10^7$ mononuclear cells/ml.) from bone marrow, peripheral or cord blood, or any other source of stem cells, is fed to the bioreactor through feed line 40a. Preferably, the peristaltic pump is operated at approximately 0.89 ml./hr. during feed of the sample to the bioreactor. The reactor should be prevented from running dry during feeding by backfilling the sample tube with a rinse solution, e.g., Iscoves Modified Dulbecco's Medium (IMDM). The pump should be run for a period sufficient to completely feed the MNF and thus saturate the activated sites on the beads with CD34 cells (or, if a sample is used which contains too few CD34 cells to entirely saturate the activated sites, to bind substantially all of the CD34 cells in the sample to activated sites, after which cells resulting from cell proliferation will bind to the remaining sites). For a sample size of 1 ml. containing approximately $5 \times 10^7$ cells, this will typically take about 3 hours.

Once the sample has been fed through the bioreactor as described in the preceding paragraph, the pump is temporarily shut off while the feed line 40a is connected to reagent reservoir 34 containing a nutrient media solution, preferably Iscove's Modified Dulbecco's Medium (IMDM), commercially available from, e.g., GIBCO BRL Products. Other nutrient media can be used; preferably the media is a defined nutrient media.

The pump is then restarted, again preferably at approximately 0.89 ml/hr, and cell proliferation is allowed to proceed continuously while the nutrient media is fed through the bioreactor.

As soon as substantially all of the activated sites on the beads are saturated, dividing cells will begin to flow out of the column with the exiting media, to be harvested in the sampler tube (or any other suitable reservoir or conduit). This continuous cell harvesting will proceed, absent mechanical failure or contamination, for the life of the column, e.g., until the reagents in the bioreactor are depleted through column erosion.

The use of the bioreactor described above is in the "continuous" mode of operation shown in FIG. 2c. To use the bioreactor in the "recycling" mode shown in FIG. 2d, it would simply be necessary to provide a conduit to route fluid from the outlet of the bioreactor back to the inlet. Because flowing the fluid through a pump may tend to deleteriously effect the cells, it may be desirable to replace the pump system with a gravity feed system, or otherwise prevent cells from being damaged during recycling.

Process Parameters

A number of parameters can be varied to affect the rate and purity of the cell output obtained during bioreactor use.

For example, the flow rate and dilution rate of the nutrient media flowing through the bioreactor during cell proliferation can be varied over a fairly broad range. Generally, it is important that the flow rate be sufficient to provide adequate oxygen to the cells, yet not so high as to wash the reagents and/or bound cells off of the beads. To optimize the volume of cell output obtained, it is preferred that the dilution rate be as high as possible without causing bound cells to be washed from the column. The relationship between dilution rate and cell concentration is described in Principles of Fermentation Technology, P. F. Stanbury & A. Whitaker, Pergammon Press, New York, 1984, at pp. 14–17.

The dimensions of the bioreactor can also be varied. The relationship between bioreactor length and width (the aspect ratio) can be varied to maximize control of process parameters.

The volume and purity of the initial sample fed into the column could also be varied.

Reagents

Coupling agents

Suitable coupling agents for binding the selective binding molecule to the bead surface are those agents that will bind the desired selective binding molecule, but will not bind undesired compounds. When the selective binding molecule is a biotinylated antibody, preferred coupling agents include avidin, streptavidin, NeutrAvidin (commercially available from Pierce Chemical, Rockford, Ill.), and other avidin derivatives. NeutrAvidin is preferred because its pI (isoelectric point) is substantially neutral and thus this protein exhibits very low non-specific binding.

Selective binding molecules

Preferred selective binding molecules are biotinylated antibodies. Other suitable selective binding molecules include cell adhesion molecules, a mix of lineage specific antigen receptors, or, if no coupling agent is used, a non-biotinylated antibody (biotinylation is only necessary in order to effect binding of the antibody to the coupling agent).

Reagents that are suitable for biotinylation of the antibody include NHS-biotin, biotin hydrazide, biotin BMCC, and other biotin derivatives. NHS-biotin is preferred, as it appears to have minimal effect on the reactivity of the antibody. Processes for biotinylation are well known. An example of a suitable process is given below in the Examples section.

Suitable antibodies include monoclonal CD34 epitopes and polyclonal CD34 or any uniquely identifiable cell surface antigen or binding site for a desired cell population. Mixtures of antibodies can also be used to enhance antibody/cell interactions, both in number and strength of the interactions, which can allow higher flow rates to be used without cells washing off of the beads.

Other reagents

A suitable rinse solution to rinse the culture column both after application of the coupling solution and after application of the biotinylated antibody is Dulbecco's PBS, pH 7.4. A suitable rinse solution to rinse the column after application of the plasma is Iscoves Modified Dulbecco's Medium (IMDM), which is also used as the nutrient media to promote cell proliferation. Other suitable rinse solutions and nutrient media are known to those skilled in the art. It may be desirable for the nutrient media to be conditioned by cell growth. The level of conditioning of the media can be enhanced by recycling the nutrient media through the chamber while concurrently removing dividing cells from the chamber.

Bioreactor Materials

The reactor components (culture column, tubing, fittings, etc.) should be autoclavable, and preferably also able to withstand gamma irradiation and other harsh methods of sterilization. Moreover, the reactor components should be compatible with tissue culture and should not leach undesirable compounds into the culture medium. The reactor parts further should not accommodate or promote adherence of cells, e.g., by lineage specific antigen receptors, cell adhesion molecules (CAMs) on the cell surface, or secretion products of the cultured cells, unless such antigens, CAMs or secretion products are specifically incorporated into the selection criteria for a given cell proliferation process.

Suitable materials that meet these criteria include polypropylene, stainless steel, polytetrafluoroethylene (TEFLON), PFA, and other inert medical grade materials well known in the art. For the tubing, silicone may in some cases be preferred for its relatively high oxygen permeability (allowing sufficient oxygen to reach the cells at lower flow rates); in other cases polytetrafluoroethylene may be preferred for its very low non-specific interaction potential.

The fittings which connect the bioreactor to other elements of the system should be able to accommodate low holdup volume, withstand minimal pressures (typically less than 10 psi), and allow for minimal constriction of flow so as to reduce channeling and adverse fluid flow patterns. Adverse fluid flow patterns could result in inadequate wetting of the column core, erosion of surface coatings on particles, or disruption of cells attached to the beads.

The beads are preferably borosilicate glass beads having epoxide groups at their surface. Such beads are commercially available from, e.g., Potters Industries, Inc., Parsippany, N.J., under the tradename Glass Spheres A and P series.

Other bead materials, e.g., polystyrene, or surface activations, e.g., carboxyl, can be used, provided that the surface of the bead is non-porous, to avoid trapping cells or other material in pores on the bead surface. The bead surface should also be sufficiently smooth to allow cells, compounds and particulate matter in the chamber to flow past the surface without adhering thereto or diffusing therein. The surface activation can be in the form of reactive groups extending from the surface of the bead due to the structure of the bead material or the manner in which the surface has been chemically treated, or can be in the form of a reactive group extending from a coating applied to the bead surface. For example, the bead could be a polypropylene or other polymer bead and the surface activation could be a crosslinked coating, e.g., of an amino acid. The reactive group is selected to be capable of binding the selected coupling agent or, if no coupling agent is used, binding the selective binding molecule itself. Preferably, the surface activation includes a sufficient number and type of binding sites to allow the beads to bind 8–12 $\mu$g NeutrAvidin per gram of beads at pH 5.0 (0.1M phosphate buffer) at room temperature during a 12–16 hour cycling process (e.g., the process shown in FIG. 5). The number of binding sites can be varied, however, to suit particular column dimensions, flow rates, or other process parameters. The bond formed with the reactive group (by the coupling agent or by the selective binding molecule, if no coupling agent is used) is typically covalent.

Preferably, the beads have a diameter of about 250–550 $\mu$m, more preferably 350–450 $\mu$m. Smaller beads, when packed in the column, may not be sufficiently far apart to allow flow of cells through the column, while larger beads may not provide sufficient available surface area to enable efficient cell interaction. The size and size distribution of the beads can be varied, however, to vary the surface area or number of binding cites available for a column having given dimensions.

In some cases, it may be desirable to include a spacer zone of non-activated beads at the top, bottom, or a specific region of the column, or mixed with the activated beads. Such a spacer zone could be used to reduce cell-to-cell interactions.

Instead of beads, any material having suitable surface activated sites could be used, provided that the material includes sufficient open space to allow flow of fluid therethrough at sufficient flow rates. Thus, the matrix could comprise a honeycomb, mesh, net, or other material having sufficient surface area and a network of connecting open spaces through which fluid can flow. Alternatively, a fluidized or magnetically stabilized bed could be configured to accomplish similar objectives.

FIG. 6 shows a system 100, in a recycle mode of operation, having both positive and negative selection elements. To provide the positive selection element, positive selection molecules can be attached to (a) the inner surface 102 of the reactor vessel, (b) the surfaces of the impeller 104 in the reactor vessel, or (c) to baffles, beads or magnetic particles inserted into the liquid in the reactor (not shown). This attachment of the positive selection molecules to a solid support allows the target population captured by the molecules to be immobilized within the liquid system. The negative selection element is provided by a shunt 106 in the recycle loop. Shunt 106 contains a selection element specific for a predetermined population other than the target population, as discussed above with reference to FIG. 1a. System 100 contains growth medium and is housed in an incubator. The system 100 is inoculated with an extract containing target cells or cells that are progenitors of the target population, and conditions are controlled to result in cell division. Cells which express positive markers for the target population are immobilized by the positive selection element, while cells which express markers not expressed on the target population are captured and removed by the negative selection element during recycling. Shunt 106 can be removed and replaced as necessary.

The following section gives an example of a therapeutic use for the target cells. The target cells can also be used in many other therapeutic and diagnostic applications.

Therapeutic Use

Figure 7:
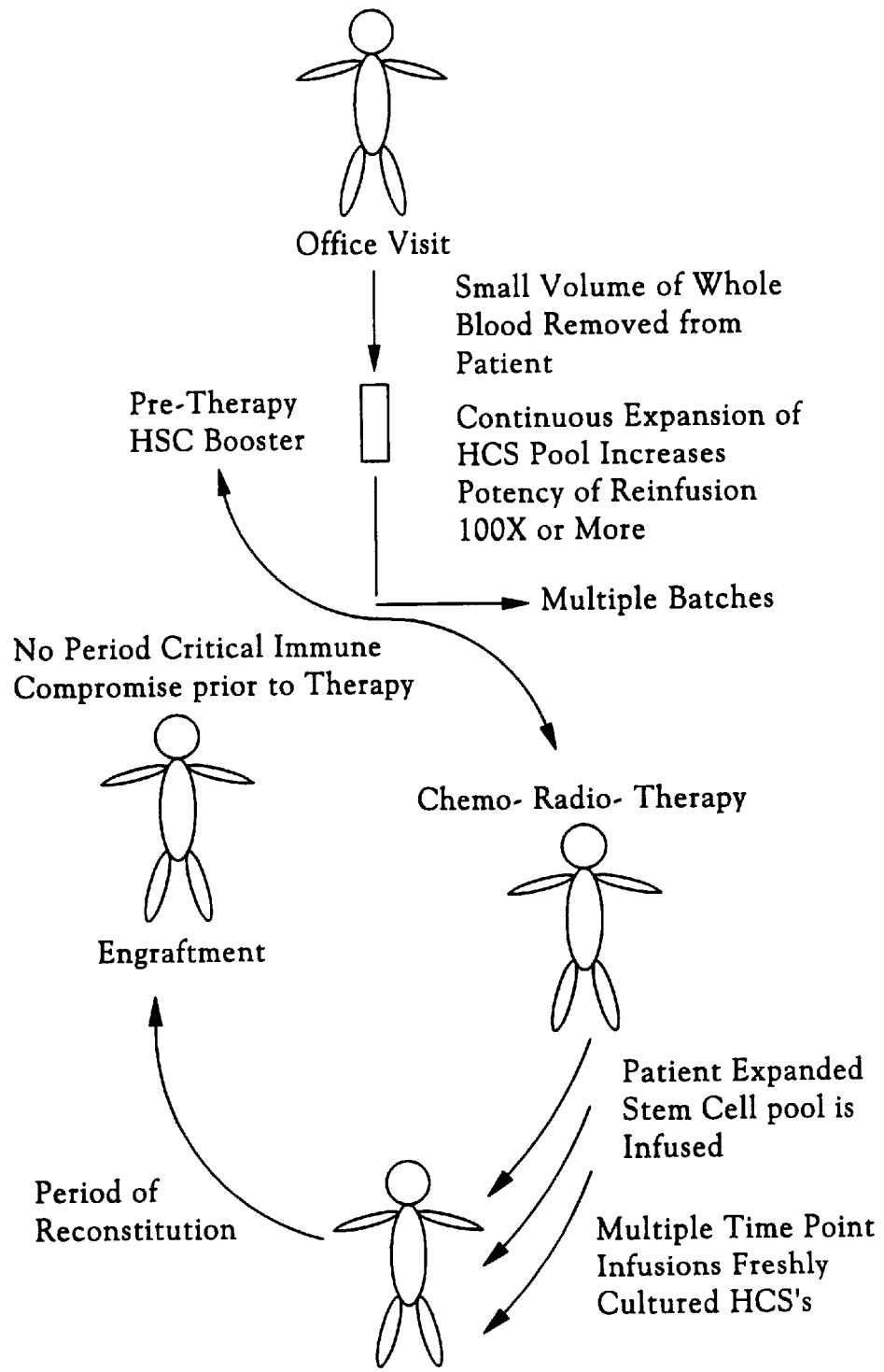
FIG. 7 is a schematic flowchart showing a method, according to one embodiment of the invention, of treating a patient with HSCs proliferated according to the invention.

As shown schematically in FIG. 7, a patient requiring immunotherapy would first have a small volume of his or her blood drawn. This blood would then be used as described above (Bioreactor Use section) to produce a pool of autologous HSCs, which would be administered to the patient as an immune system booster prior to a treatment damaging the patient's immune system and/or blood forming system (e.g., chemotherapy), and/or as a stimulant to the patient's compromised immune or blood forming system after the treatment.

Alternatively, a cell sample could be used to produce a pool of a selected population of differentiated cells, by charging the cells to a bioreactor of the invention and supplying to the bioreactor one or more growth factors selected to cause the cells to differentiate to cells of the selected population.

EXAMPLES

Example 1

CD34 HPCA-2 (Human Progenitor Cell Antigen 2) was biotinylated with NHS-Biotin using the following procedure:

Dialyzed 1 ml. of a 25 tg/ml stock solution of antibody against 1500 ml. of a dialysis buffer, e.g., 50 mM bicarbonate buffer pH 8.5, in a DIALYZER SLIDE dence (Pierce Chemical, Rockford, Ill.) for 12–16 hours. Immediately before using, dissolved 1 mg of the NHS-biotin in 75 µl DMSO. Added 25 µl of this solution to the dialysate. Incubated at room temperature for 1 hour. Transferred to a CENTRICON-30 microconcentrator (Amicon) and spun at 14,000 cgf for 12 minutes to remove unreacted biotin. Recovered the retentate in a 1.5 ml Eppendorf tube. Brought the volume up to 1.5 ml with Dulbecco's PBS. Stored in the dark at about 4° C. and used within one day.

A bioreactor, as shown in FIG. 3, was then assembled as follows:

1. Using a standard one-hole paper punch (0.25" punch), two 0.25" diameter grids were cut from 210 µm polypropylene mesh. Carefully placed the grids into the 0.508 cm orifices of two stainless steel reducing unions. Used 0.508 OD PFA tubing to guide the grid into place at the inner lip of the reducer.
2. Cut a 5 cm length of 0.508 cm OD PFA tubing (PFA-T4-062-100, Cambridge Valve and Fitting) using a razor blade, taking care to make a perpendicular cut so that the tubing would lay flush against the grid in the reducer.
3. Assembled one of the reducing unions onto one end of the length of tubing, using a TEFLON front and back ferrule arrangement.
4. Loaded approximately 0.55 grams (+/−0.05 grams) of epoxy activated borosilicate glass beads into the bioreactor, making certain that the beads completely filled the tubing, so that no unnecessary voids were present.
5. Installed the other reducing union and front and back ferrule at the other end of the tubing, seated ends and finger tightened.
6. Installed a 2 cm length of 0.318 OD PFA tubing (PFA-T4-062-25, Cambridge Valve and Fitting) and a TEFLON polymor front and back ferrule at each 0.318 ID end of the reducing union. Finger tightened.
7. Installed a 50 cm length of #13 Pharmed tubing (H-06485-13, Cole-Parmer) onto each 0.318 OD PFA tubing, resulting in a closed, autoclavable loop.
8. Hand tightened all fittings. Autoclaved the bioreactor at 121° C. for 30 minutes with a 15 minute dry goods exhaust. Upon removal from the autoclave, transferred the bioreactor to an 80° C. drying oven for about 3 hours to remove residual moisture.
9. Allowed the bioreactor to cool and re-tightened all fittings with a wrench.
10. Placed the bioreactor on a stand and loaded the #13 Pharmed tubing into a peristaltic pump.

Figure 5A:
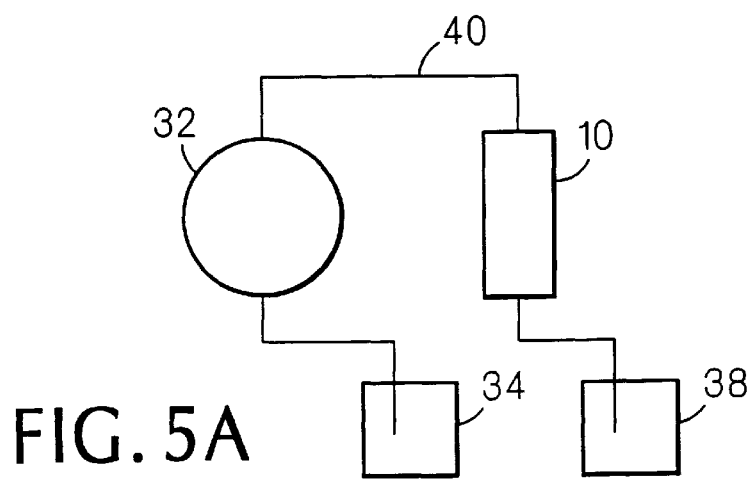
FIG. 5a is a schematic diagram showing the bioreactor during a rinse cycle subsequent to cycling with reagent.

Next, the bioreactor was loaded with reagents (Bioreactor Set-Up) as follows:

1. Using scissors, the #13 Pharmed Tubing was cut approximately 5 cm from the lower outlet of the bioreactor. The unsheathed end of a 1"21 gauge Vacutainer Collection Needle was inserted into each of the freshly cut ends of the #13 tubing. The sheath was then removed from the other end of the needles and used to puncture the top of a 1.5 ml Eppendorf Microfuge tube containing 1.5 ml of a coupling solution (100 µg NeutrAvidin in pH 5.0 phosphate buffer (0.1M) made and filter sterilized (0.2 µm) immediately prior to use). This procedure results in the system configuration shown in FIG. 5.
2. Started the peristaltic pump at 50% pump output (0.89 ml/hr.) so that the coupling solution was pumped up through the bioreactor, thus reducing the likelihood of air entrapment which could produce adverse channeling effects. After about half the liquid volume had been reduced, added an additional 0.5 ml of the coupling solution to ensure that the bioreactor would be adequately supplied with solution during the entire coupling procedure. Allowed the coupling solution to recycle through the system loop for 16 hours.
3. Stopped the pump and reconfigured as shown in FIG. 5a as follows: Changed pump directional control to allow solution to be pumped down. Broke the recycle loop, being careful not to introduce air, by removing one end from the 1.5 ml Eppendorf tube. Attached this end into a presterilized feed bottle containing a rinse solution (20 ml of Dulbecco's PBS pH 7.4). Primed the feed bottle using a luer lock syringe to apply positive pressure on the sterile exhaust filter. Removed the other end from the Eppendorf tube and installed it onto a pre-sterilized waste bottle.
4. Started the pump at 50% pump output (0.89 ml/hr.) and rinsed the bioreactor with rinse solution for 3 hours.
5. Stopped the pump. Reconfigured as shown in FIG. 5 by transferring the feed and waste lines to the 1.5 ml of NHS-CD34 biotinylated antibody solution prepared above. Started the pump at 50% pump output and ran it in this configuration for 6 hours.

6. Stopped the pump and repeated the reconfiguration and rinse cycle described in step 3 above.

7. Stopped the pump. Reconfigured as shown in FIG. 5, placed a 1.5 ml Eppendorf tube containing 1.5 ml of autologous blood plasma into the recycle loop. Started the pump at 50% output and recycled for 6 hours.

8. Stopped the pump.

The pump was then reconfigured for cell proliferation, i.e., to the configuration shown in FIG. 4. Step 3 was then repeated, replacing the rinse solution with 1 liter of Iscoves Modified Dulbecco's Medium (IMDM).

Cell proliferation then proceeded as follows:

1 ml of fresh Ficoll-Paque Gradient Purified Mononuclear Fraction (MNF) from peripheral blood was resuspended in HBS at approximately $5 \times 10^7$ mononuclear cells/ml. Attached the MNF to the feed line but otherwise remained in the configuration shown in FIG. 4. Started the pump at 50% output. As the MNF was fed into the bioreactor, the cells were kept in suspension to reduce the potential for clotting or clogging. To prevent the pump from running dry, backfilled the Eppendorf with IMDM for several hours. Did not stop the pump for at least 3 hours after starting the MNF through the bioreactor. Stopped the pump and reinstalled the feed line to the IMDM reservoir. Placed the sampler tube as shown in FIG. 4. Restarted the pump at 50% output. Exchanged the sampler tube daily for analysis by hemocytometer, phase and fluorescence microscopy.

Figure 9:
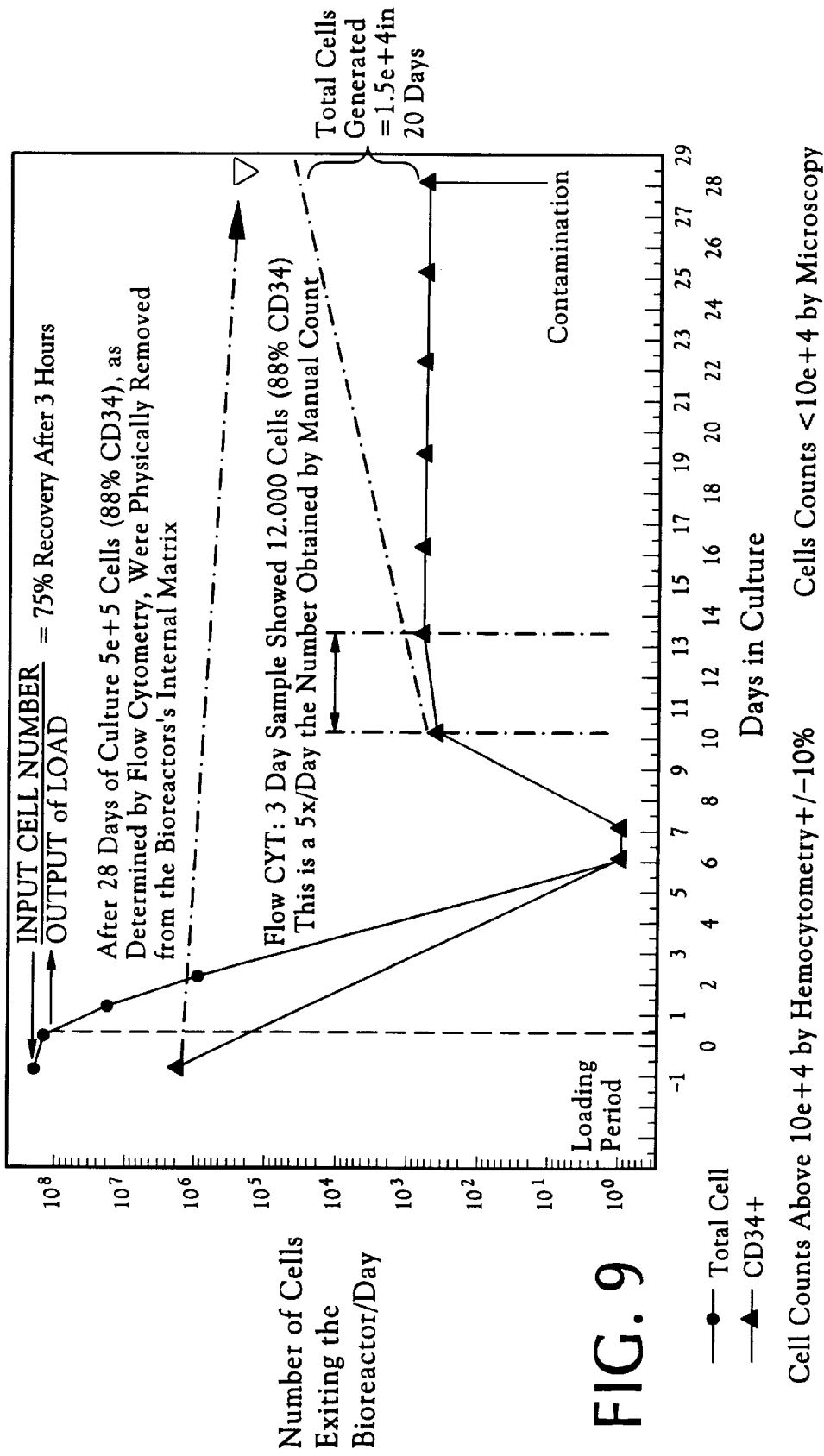

The following results, illustrated graphically in FIG. 9, were obtained from the cell proliferation process using the peripheral blood sample:

MNF passed through the bioreactor=$5 \times 10^7$ mononuclear cells/ml.

MNF recovered in filtrate after 3 hours=$3 \times 10^7$ mononuclear cells/ml. (Note that mononuclear cells continued to appear in the filtrate for 3–5 days after the initial loading. This ended after about 5 days. Included in these fractions were some CD34+ cells which were either loosely bound or large in size, or were in the process of dividing when introduced to the column. Only strongly bound CD34+ population remained in the reactor at 50% pump output.)

During the period from 5 days after inoculation to 8 days after inoculation, substantially no CD34 cells left the bioreactor, indicating that the strongly bound CD34 cells left after the initial 5 day period were remaining on the column and cell proliferation was not yet detectable.

From 8 days after the initial inoculation until bioreactor failure, roughly 100–500 CD34+ cells per day (measured by manual microscopy) appeared in the sampler tube. (The average number of cells collected per day over the life of the column was 350 cells/day. This number is shown in FIG. 9 as the number collected each day, as it appeared that deviation from the average number as merely the result of inaccuracies in the manual counting procedure used.) The harvested cells had a birth diameter of 5+/−2 μm, much smaller than the CD34 cells which were immobilized on the beads in the bioreactor, the diameters of the vast majority of which ranged nominally from about 10 μm to 15 μm. The cell type and relative frequency remained constant for 21 days before the bioreactor succumbed to mechanical failure.

Example 2

The procedures described in Example 1 were repeated, substituting cord blood for the peripheral blood in the cell proliferation process.

The following results, shown in FIG. 9a, were obtained from the cell proliferation process:

MNF passed through the bioreactor=$5 \times 10^7$ mononuclear cells/ml.

MNF recovered in filtrate after 3 hours=$3 \times 10^7$ mononuclear cells/ml. (As noted above, mononuclear cells continued to appear in the filtrate for 3–5 days after the initial loading.)

From 8 days after the initial inoculation until bioreactor failure, as shown in FIG. 9a, roughly 500–1000 CD34 + cells/day (measured by manual microscopy), with a birth diameter of 5+/−2 μm, appeared in the sampler tube. The average number of cells collected per day was 750, and, for the reasons explained above in Example 1, this is the number that is shown for each day in FIG. 9a. Measured by flow cytometry, a sample taken from the sampler tube for the period between 10 days and 13 days (3 day period) contained 12,000 cells, of which 88% were CD34+ cells. The cell type and relative frequency remained constant for 28 days before the bioreactor succumbed to contamination.

Example 3

Figure 8:
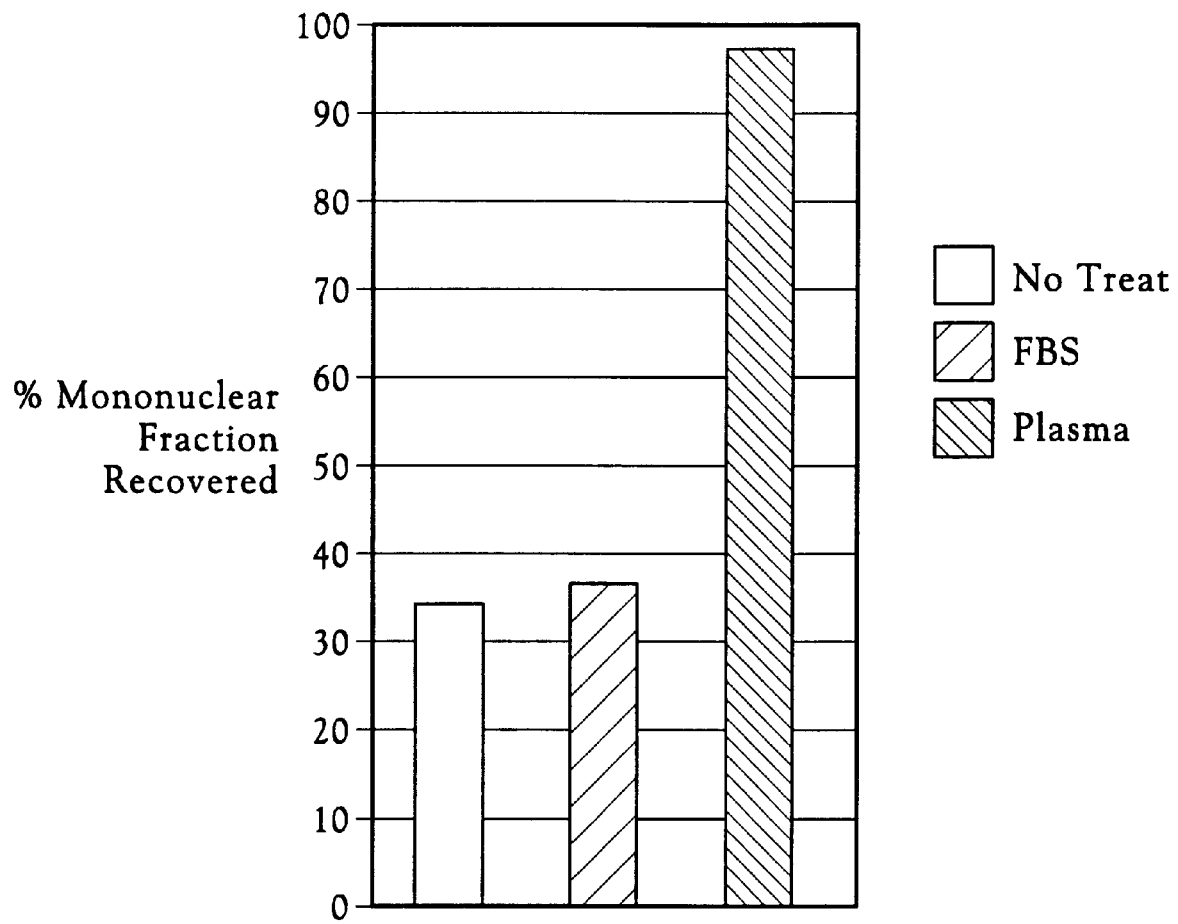
FIG. 8 is a graph illustrating the effect on nonspecific interaction of treating the bead surface with, alternatively, plasma or fetal bovine serum.

The effect of treating the bead surface with plasma, or, alternatively, fetal bovine serum, on non-specific interaction at the bead surface was studied. Cord blood was centrifuged under a density gradient (Ficoll-Paque), the mononuclear fraction (MNF) was removed and concentrated to $1 \times 10^6$ cells in a 10 μl volume. The sample was then injected under flow conditions of 0.89 ml/hr via a septum into a bioreactor which had been prepared as described in Example 1, steps 1–7, using cross-matched human plasma in step 7. This procedure was repeated using a bioreactor that had been prepared as described in the same manner, except that fetal bovine serum (FBS) was substituted for cross-matched human plasma in step 7. The procedure was then repeated again using a bioreactor that had been prepared as described in Example 1, steps 1–6 (no plasma or FBS treatment). Cells exiting the reactor in each case were counted in a time-wise fashion. The resulting concentration profile was then integrated to obtain the percent of cells recovered. Recovery increases as nonspecific interactions decrease, and thus the results of this experiment, shown in FIG. 8, illustrate that non-specific interactions were greatly reduced by treating the bioreactor with plasma, but not significantly reduced by treating the bioreactor with FBS.

Example 4

POSITIVE (+) SELECTIVE CLONOGENIC EXPANSION IN A SEMI-BATCH CULTURE Positive Selection (FIG. 1): The population selected by the selection element was the predetermined target population. In this case the target population was composed of CD34 cells. Growth Medium: Iscove's Modified Dulbecco's Medium (IMDM) (100 ml), Pen/Strep (50 μl), BSA (50 mg/ml), Insulin (50 ug/ml), Transferrin (1 mg/ml), Low Density Lipoprotein (100 μl), 2-Mercapto-Ethanol (7 μl of 1/100 solution), Flt3 (100 ng/ml), SCF (100 ng/ml), and IL-3 (20 ng/ml).

1. Obtained a Cord Blood extract containing CD34 cells.
2. Separated the Mononuclear Fraction (MNF) by Ficoll Density Gradient Centrifugation.
3. Inoculated the 4 ml culture medium with $1 \times 10^6$ Mononuclear Cells (MNCs)/ml.
4. Placed the culture plate in an incubator at 37° C. and 5% $CO_2$.
5. On day 7 harvested the culture and purified by positive (+) selection (see description of positive selection procedure below) for CD34 cells while saving the culture medium for step 7.
6. Split the culture medium in half. Discarded one half and replenished the other half with an equal volume of fresh culture medium.

7. Returned the positive (+) selection containing CD34 cells to the culture medium prepared in step 5 and placed the culture plate in an incubator at 37° C. and 5% $CO_2$.

8. For one selection cycle using the specified medium harvested between day 10 and day 15.

9. For multiple cycles of selection repeated steps 5 through 7 each 1 to 30 days.

Positive (+) Selection Procedure (Step 5, above; shown in FIG. 1): We incubated the cells in the culture with a cocktail containing a biotintylated antibody to the predetermined target population such as biotintylated CD34, c-kit, Lectin, etc. To this suspension Avidin was added and allowed to bind the biotintylated antibody. This later suspension was thoroughly rinsed to remove any biotintylated antibody/Avidin complex that was not interacting with the target population. To this rinsed solution a biotintylated dextran/iron complex was added. The biotintylated dextran/iron complex reacted with the Cell/Biotintylated antibody/Avidin complex. This solution was then passed between a strong magnet. The predetermined target population was captured in the magnetic field which was later removed to allow simple harvest of the positively selected population. This procedure is described in further detail below:

Materials and Supplies

Sterile Dulbecco's Physiological Buffered Saline (PBS) with 4% Fetal Calf Serum (FCS) without Magnesium or Calcium 1.25 μg/μl Biotintylated CD34 (BD) in DPBS with 4% FCS 1.25 μg/μl Avidin (Pierce) in DPBS with 4% FCS Biotintylated Dextran/Iron Complex (Miltenyi) Solution Column (Stem Cell Technologies)

Magnet (Stem Cell Technologies)

Peristaltic Pump

Biological Safety Cabinet (BSC)

15 ml Polypropylene Tube

37° C./5% $CO_2$ Incubator

4° C. Refrigerator

Iscove's Modified Dulbecco's Medium (IMDM) with 10% FCS

Table Top Centrifuge

Culture initiated as described above.

1. Removed a growing (as described above) culture of hematopoietic cells from the 37C./5% $CO_2$ incubator. Spun down the culture at 1000 RPM at 4° C. for 10 minutes to pellet the cells. Saved the supernatant medium for reuse. Resuspended the pellet in 0.3 ml IMDM with 10% FBS.

2. To this suspension added 100 μl of the biotintylated antibody solution and 100 μl of the Avidin solution and refrigerated at 4° C. for 30 minutes with occasional gentle mixing.

3. Added 5 ml of IMDM with 10% FBS to the suspension and mixed gently. Centrifuged at 1000 rpm for 10 minutes at 4° C. Removed and discarded the supernatant.

4. Resuspended the pellet in 0.5 ml of IMDM with 10% FBS. To this solution added 100 μl of the biotintylated dextran/iron complex and incubated at 4° C. for 30 minutes with occasional gentle mixing.

5. Pre-rinsed the column in once in DPBS followed by 10 column volumes (25ml) of DPBS with 4% FCS at a flow rate of 2 ml/minute. After placing the column within the magnetic field, applied the cell suspension to the top of the column and began pumping the solution through the column at the above rate. Kept adding fresh IMDM with 10% FBS over the original solution so the column did not at any time dry out.

6. After roughly 25 mls had passed since the cell suspension was added, changed the collection tube and removed the column from the magnet. Continued to add fresh IMDM as in step 5 until 25 mls has been collected. This fraction contained the positively selected predetermined target population.

7. Spun down the collected fraction (retentate). Removed and discarded this supernatant. Resuspended the pellet in half the original conditioned medium. Refreshed the remaining half volume with new growth medium as described above and returned to the 37° C. incubator.

Example 5

NEGATIVE (−) SELECTIVE CLONOGENIC EXPANSION IN A SEMI-BATCH CULTURE Negative Selection (FIG. 1a): The population selected by the selection element did not include the predetermined target population. In this case the target population was CD34+ cells.

Growth Medium: Iscove's Modified Dulbecco's Medium (IMDM) (100 ml), Pen/Strep (50 μl), BSA (50 mg/ml), Insulin (50 μg/ml), Transferrin (1 mg/ml), Low Density Lipoprotein (100 μl), 2-Mercapto-Ethanol (7 μl of 1/100 solution), Flt3 (100 ng/ml), SCF (100 ng/ml), and IL-3 (20 ng/ml).

1. Obtained an Umbilical Cord Blood extract containing CD34+ cells.

2. Separated the Mononuclear Fraction (MNF) by Ficoll Density Gradient Centrifugation.

3. Inoculated the 4 ml culture medium with $1 \times 10^6$ Mononuclear Cells (MNCs)/ml.

4. Placed the culture plate in an incubator at 37° C. and 5% $CO_2$.

5. On day 7, harvested the culture and purified by negative (−) selection, as described below, for CD34+ cells while saving the culture medium for step 7.

6. Split the culture medium in half. Discarded one half and replenished the other half with an equal volume of fresh culture medium.

7. Returned the negative (−) selection containing CD34+ cells to the culture medium prepared in step 5 and placed the culture plate in an incubator at 37° C. and 5% $CO_2$.

8. For one selection cycle using the specified medium, harvested between day 10 and day 15.

9. For multiple cycles of selection repeated steps 5 through 7 each 1 to 30 days.

Negative (−) Selection Procedure (Step 5 above; shown in FIG. 1a): We incubated the cells in the culture with a cocktail containing selection molecules (antibodies to T-cell surface antigens) linked to an anti-dextran molecule. The cell suspension was then passed through a column containing glass beads coated with dextran. Cells with no antibody/anti-dextran were allowed to pass through the column and were collected as the predetermined target population while those which complexed were captured.

Materials and Supplies

⅜ inch TEFLON polymer approximately 2" in length

⅛ inch TEFLON tubing approximately 2" in length

⅛ inch ID flexible TYGON polymer tubing approximately 1" in length

⅜ to ⅛ inch Stainless Steel Reducer with TEFLON polymer ferrule Inserts

⅜ inch diameter Polypropylene Mesh with gridded 210 um openings 1 gram of Epoxy Glass Beads 425 um nominal diameter $dH_2O$ 10 gram of Dextran (Sigma, Tissue Grade)

10 ml 0.1M pH 5.0 Sodium Phosphate Buffer

Sterile Dulbecco's Physiological Buffered Saline (DPBS) with 4% Fetal Calf Serum (FCS) without Magnesium or Calcium Antibody/anti-dextran cocktail composed of the following selection molecules:
CD2, CD3, CD14, CD16, CD19, CD24, CD56, CD66b and glycophorin A at concentrations between 0.5 and 1.25 μg/μl each.
Ring Stand
Tubing Clamp
Autoclave
Biological Safety Cabinet (BSC)
15 ml Polypropylene Tube
Sterile Filter and Syringe
37° C./5% $CO_2$ Incubator
4° C. Refrigerator
Iscove's Modified Dulbecco's Medium (IDMM) with 10% FCS
Table Top Centrifuge
Culture initiated as described above.

1. Assembled the ⅜" and ⅛" TEFLON polymer tubes with one reducing nut complete with TEFLON polymer tubes. Prior to inserting the ⅜" TEFLON polymer tube, placed the polypropylene grid between the tubing and the inner flange of the fitting. Hand tightened the fitting, installed the 1/16" ID TYGON polymer tubing and on the ⅛" OD TEFLON polymer tubing and wraped loosely with foil to autoclave with preparation in step 2. (Note: one end of the tubing has no reducing nut.)

2. Weighed out 1 gram of epoxy glass beads into a 15 ml polypropylene tube. Submersed the beads in about 2 ml of $dH_2O$. Loosely installed the cap and placed in the autoclave with contents of step 1.

3. After autoclaving, transferred the sterile materials from steps 1 and 2 to the Biological Safety Cabinet.

4. Prepared a sterile dextran solution by adding 2 grams of dextran to 10 mls of the pH 5 Phosphate Buffer (0.1M) and sterile filtering through a syringe.

5. Removed the $dH_2O$ from the beads and replaced the liquid contents with approximately 2 ml of the sterile dextran solution. Allowed this solution to incubate at 37° C. for at least four hours.

6. Removed the sterile dextran solution and with repeat rinses replaced the dextran solution with sterile DPBS containing 4% FCS. Allowed this solution to incubate for about 90 minutes at room temperature.

7. Unwrapped the column assembly and installed a tubing clamp onto the 1/16" TYGON polymer tubing. Tightened the clamp to completely restrict the pathway. Perpendicular to the working surface, clamped the column so that the end with the reducing nut, ⅛" TEFLON polymer tubing, 1/16" TYGON polymer tubing and tube clamp aimed downward.

8. Using a pipette, transferred the DPBS solution containing the Dextran coated Glass Beads into the top, open end, of the column assembly. Adjusted the tube clamp so that the liquid flowed down through the column.

9. Washed the column with approximately 3 ml of IDMM with 10% FBS. The column was now ready to receive cells.

10. Removed a growing (as described above) culture of Hematopoietic cells from the 37° C./5% $CO_2$ incubator. Spun down the culture at 1000 RPM at 4° C. for 10 minutes to pellet the cells. Saved the supernatant medium for reuse. Resuspended the pellet in 1 ml IDMM with 10% FBS.

11. To this suspension added 200 μl of the antibody/anti-Dextran cocktail and refrigerated at 4° C. for 30 minutes with occasional gentle mixing.

12. Applied the suspension to the column prepared in steps 1–9, collecting the permeate below in a 15 ml polypropylene centrifuge tube.

13. Rinsed the suspension with at least 3 ml of IDMM with 10% FBS while continuing to collect the permeate.

14. Centrifuged the permeate. Removed and discarded this supernatant. Resuspended the pellet in half the original conditioned medium. Refreshed the remaining half volume with new growth medium as described above and returned to the 37° C. incubator.

Results of Examples 4 and 5

Figure 11:
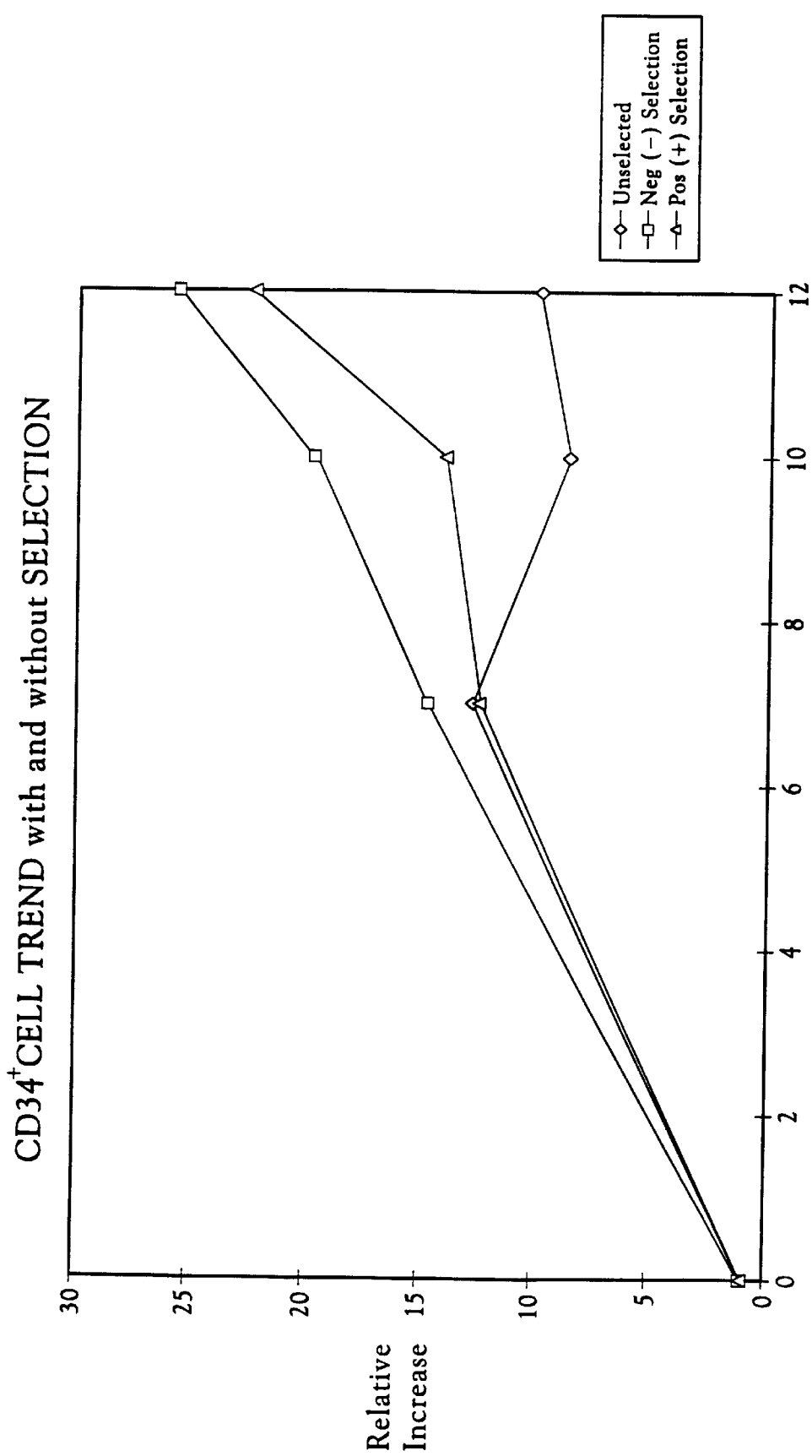
FIGS. 11 and 11a are graphs illustrating the increase in CD34+ cells and leukocytes, respectively, in the experiments described in Examples 4 and 5.
Figure 11A:
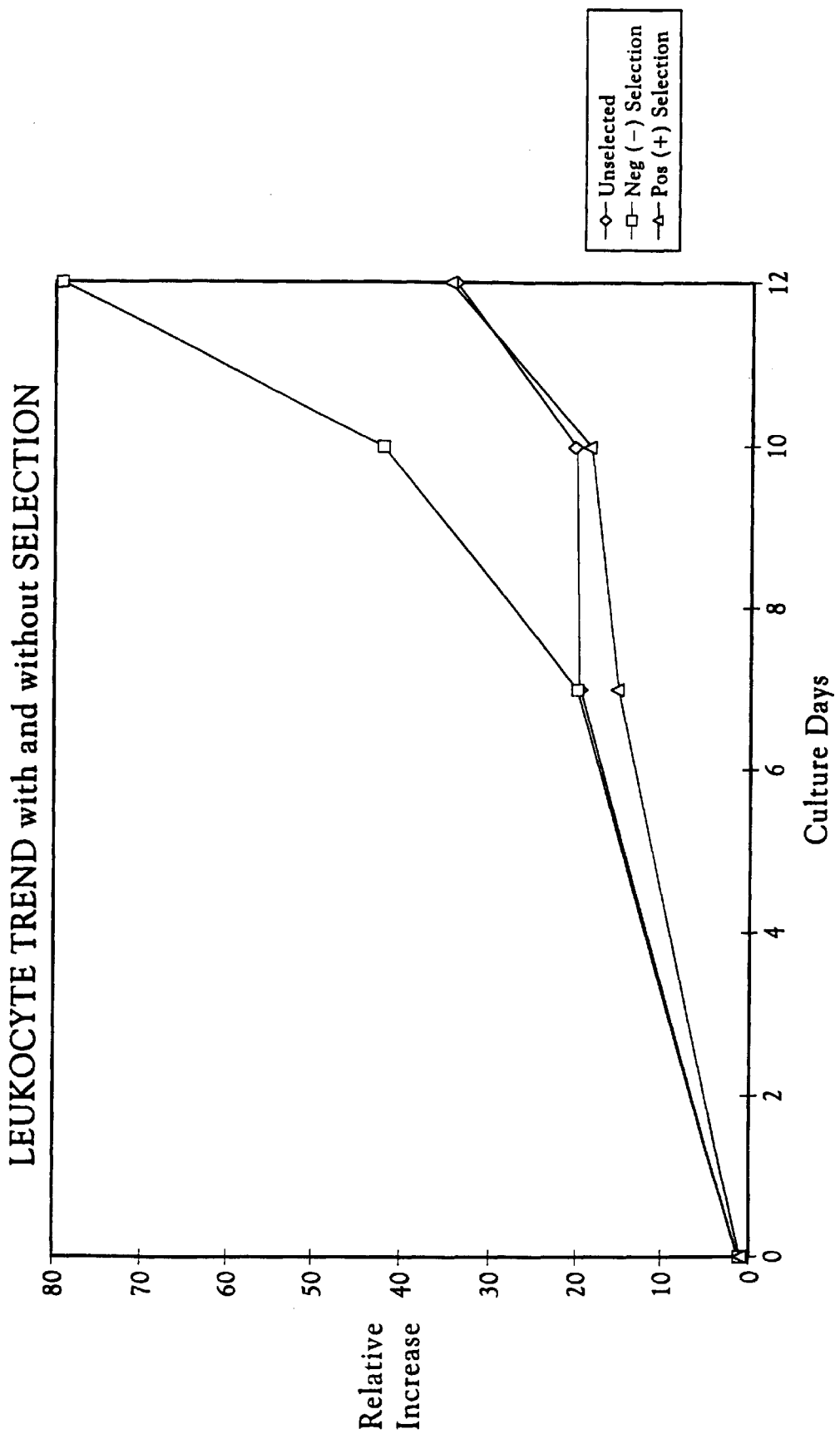

The results of the experiments performed in Examples 4 and 5 are shown graphically in FIGS. 11 and 11a. FIG. 11 represents the relative increase in CD34+ cells in duplicate samples of a representative cord blood extract. All data points are from the same extract. All cultures were manipulated on day 7 in this experiment. The unselected sample was split and replenished with ½ fresh medium to mimic medium conditions in the other samples. Inefficiencies in the separation procedures have been accounted for. FIG. 11a shows the relative increase in leukocytes under the same conditions in the same experiment.

Other Embodiments

Other embodiments are within the following claims.

Figure 10:
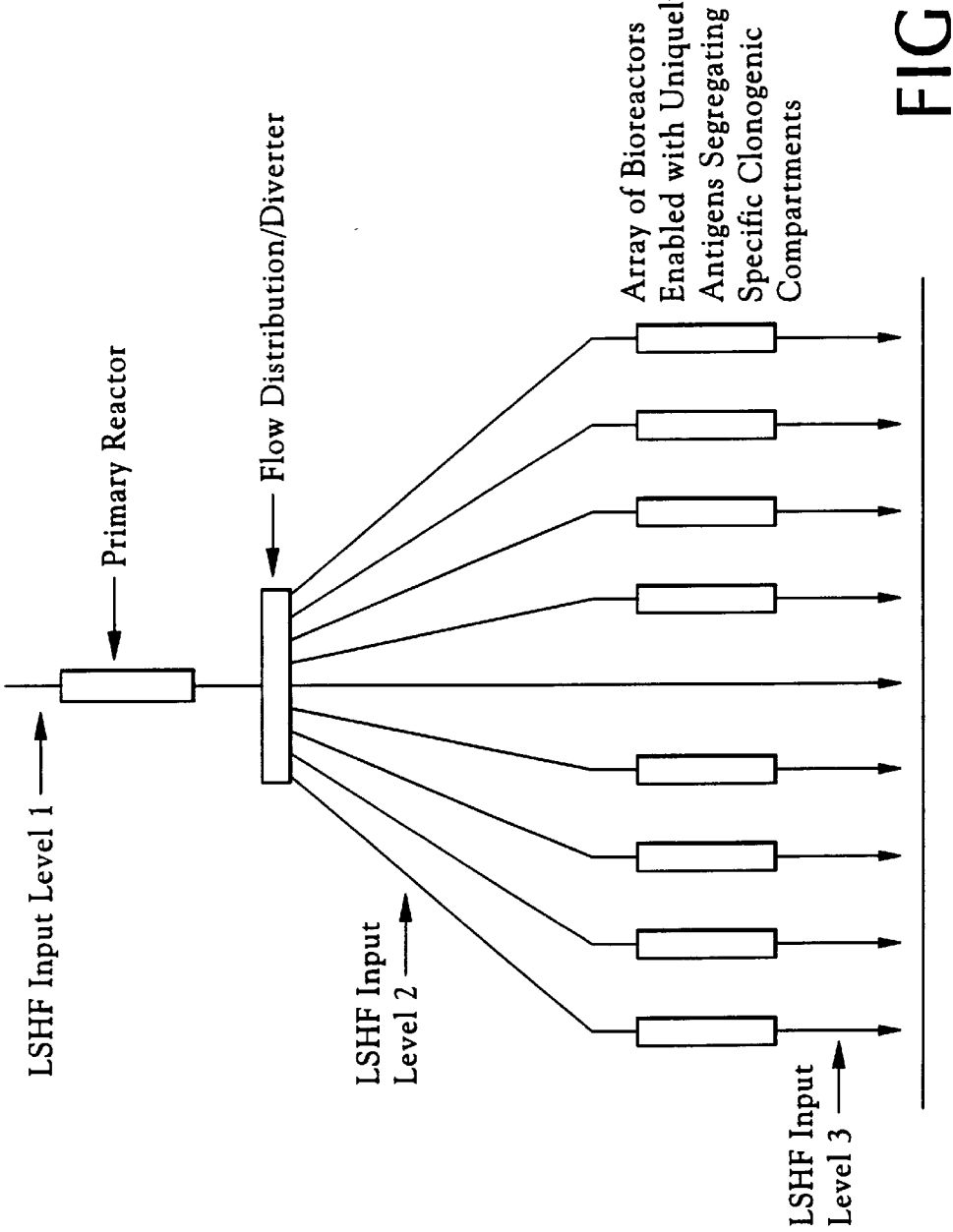
FIG. 10 is a schematic illustration of a plurality of bioreactors of the invention arranged in series to allow the cells harvested from one bioreactor to be expanded, differentiated, or used to produce a cell by-product in another bioreactor downstream therefrom.

For example, while the method of the invention has been described in connection with the expansion of a population of relatively undifferentiated cells, preferably HSCs, the method and system can be used to expand other cell populations. As shown in FIG. 10, relatively differentiated cells could be expanded, e.g., in a bioreactor downstream from a bioreactor used to expand HSCs. While most or all differentiated cells are not renewable, the cells could be expanded for a limited number of generations, or, if the cells are renewable, conceivably for as many expansions as are possible for HSCs.

We claim:

1. A method of selective expansion of a target population of cells that are suitable to be infused into a human patient, said method comprising:

(a) introducing a starting sample of cells, containing cells of the target population or a progenitor to the target population, into a growth medium;

(b) causing cells of the target cell population to divide; and (c) concurrently with, intermittently during or following step (b), contacting the cells in the growth medium with a selection element, comprising a plurality of selective binding molecules with specific affinity either for target cells or for a first population of non-target cells, so as to select cells of the target population from other cells in the growth medium.

2. The method of claim 1 wherein said selective binding molecules are specific for said target cells.

3. The method of claim 1 wherein said selective binding molecules are specific for non-target cells.

4. The method of claim 2, further comprising, prior to step (a), contacting said starting sample of cells with a selection element comprising selective binding molecules with specific affinity for a second population of non-target cells.

5. The method of claim 1, further comprising removing cells from said growth medium.

6. The method of claim 5, wherein the removed cells are cells of said target cell population.

7. The method of claim 5 wherein the removed cells are non-target cells.

8. The method of claim 1 wherein said starting sample of cells includes said target cells, and said expansion is clonogenic.

9. The method of claim 1 wherein said starting sample of cells includes progenitors of said target cells.

10. The method of claim 1, further comprising removing the growth medium prior to said contacting step.

11. The method of claim 1, wherein said selection element comprises a solid support to which said selective binding molecules are bound.

12. The method of claim 11 wherein said growth medium is disposed in or caused to flow through a chamber.

13. The method of claim 12 further comprising causing said growth medium to recycle through said chamber, flowing from an inlet, through said chamber, to an outlet of said chamber, and returning from the outlet to the inlet via a conduit.

14. The method of claim 2 wherein said selective binding molecules bind to a cell surface antigen on cells of said target cell population but not on cells not in said target cell population.

15. The method of claim 14 wherein said selective binding molecule is a biotinylated antibody specific for an antigen on the surfaces of said cells of said target cell population.

16. The method of claim 3 wherein said selective binding molecules bind to a cell surface antigen that is on cells of the non-target cell population but not on cells of said target cell population.

17. The method of claim 11 further comprising the step of causing plasma to bind to regions of said solid support on which selective binding molecules are not present.

18. The method of claim 17 wherein said plasma is autologous plasma.

19. The method of claim 17 wherein said plasma is a type-matched allogeneic plasma.

20. The method of claim 11, further comprising the step of contacting the solid support with an agent that is capable of binding to regions of said solid support on which said selective binding molecules are not present to prevent non-specific interaction between said regions and materials contacting said solid support.

21. The method of claim 1 wherein said growth medium is conditioned by cells present in the growth medium.

22. The method of claim 21 further comprising causing the growth medium to recycle through a fluid flow loop, thereby enhancing the level of conditioning.

23. The method of claim 22 further comprising concurrently removing dividing cells from the fluid flow loop during recycling.

24. The method of claim 1, further comprising regulating the oxygen saturation of the growth medium to be from 0% to 20% relative to the solubility of oxygen in said fluid at equilibrium with air at 37° C. and 1 atm pressure.

* * * * *